United States Patent
Doisaki et al.

(10) Patent No.: US 11,034,643 B2
(45) Date of Patent: Jun. 15, 2021

(54) HIGHLY UNSATURATED FATTY ACID OR HIGHLY UNSATURATED FATTY ACID ETHYL ESTER WITH REDUCED ENVIRONMENTAL POLLUTANTS, AND METHOD FOR PRODUCING SAME

(71) Applicant: NIPPON SUISAN KAISHA, LTD., Tokyo (JP)

(72) Inventors: Nobushige Doisaki, Tokyo (JP); Kazuhiko Hata, Ibaraki (JP); Shinji Tokiwa, Ibaraki (JP); Kazunori Matsushima, Tokyo (JP)

(73) Assignee: NIPPON SUISAN KAISHA, LTD., Tokyo (JP)

(*) Notice: Subject to any disclaimer, the term of this patent is extended or adjusted under 35 U.S.C. 154(b) by 0 days.

(21) Appl. No.: 16/514,191

(22) Filed: Jul. 17, 2019

(65) Prior Publication Data

US 2019/0337883 A1 Nov. 7, 2019

Related U.S. Application Data

(60) Continuation of application No. 15/366,522, filed on Dec. 1, 2016, now Pat. No. 10,399,922, which is a division of application No. 14/400,652, filed as application No. PCT/JP2013/063425 on May 14, 2013, now Pat. No. 9,540,306.

(30) Foreign Application Priority Data

May 14, 2012 (JP) ................................ 2012-110809

(51) Int. Cl.
| | | |
|---|---|---|
| C07C 69/587 | (2006.01) |
| C07C 67/03 | (2006.01) |
| C07C 67/54 | (2006.01) |
| C07C 67/56 | (2006.01) |
| C07C 51/47 | (2006.01) |
| C07C 57/03 | (2006.01) |
| C11C 3/00 | (2006.01) |
| A23D 9/02 | (2006.01) |
| C11B 3/12 | (2006.01) |
| A23L 33/115 | (2016.01) |
| A61K 31/20 | (2006.01) |
| A61K 31/202 | (2006.01) |
| A61K 31/232 | (2006.01) |
| B01D 3/14 | (2006.01) |
| B01D 15/32 | (2006.01) |
| C07C 51/44 | (2006.01) |
| C11B 3/16 | (2006.01) |

(52) U.S. Cl.
CPC ........... *C07C 69/587* (2013.01); *C07C 51/47* (2013.01); *C07C 57/03* (2013.01); *C07C 67/03* (2013.01); *C07C 67/54* (2013.01); *C07C 67/56* (2013.01); *A23D 9/02* (2013.01); *A23L 33/115* (2016.08); *A61K 31/20* (2013.01); *A61K 31/202* (2013.01); *A61K 31/232* (2013.01); *B01D 3/143* (2013.01); *B01D 15/325* (2013.01); *C07C 51/44* (2013.01); *C11B 3/12* (2013.01); *C11B 3/16* (2013.01); *C11C 3/003* (2013.01)

(58) Field of Classification Search
CPC .............................. C07C 69/587; C07C 57/03
See application file for complete search history.

(56) References Cited

U.S. PATENT DOCUMENTS

| | | | | |
|---|---|---|---|---|
| 5,215,630 A | * | 6/1993 | Hata | .............. B01D 3/146 203/38 |
| 5,502,077 A | * | 3/1996 | Breivik | ................. A61K 31/20 514/560 |
| 5,840,944 A | | 11/1998 | Furihata et al. | |
| 5,945,318 A | | 8/1999 | Breivik et al. | |
| 6,469,187 B1 | | 10/2002 | Craven et al. | |
| 7,718,698 B2 | | 5/2010 | Breivik et al. | |
| 8,258,330 B1 | | 9/2012 | Harting Glade et al. | |
| 8,586,772 B2 | * | 11/2013 | Harting Glade | .......... C11C 1/08 554/170 |

(Continued)

FOREIGN PATENT DOCUMENTS

| | | |
|---|---|---|
| CN | 1222564 | 7/1999 |
| EP | 0610506 A1 | 8/1994 |

(Continued)

OTHER PUBLICATIONS

USPTO Final Office Action corresponding to U.S. Appl. No. 14/400,652; dated Mar. 4, 2016.

(Continued)

*Primary Examiner* — Yate' K Cutliff
(74) *Attorney, Agent, or Firm* — Cantor Colburn LLP

(57) ABSTRACT

A highly unsaturated fatty acid or a highly unsaturated fatty acid ethyl ester that has been produced using as a feedstock oil a fat or oil that contains highly unsaturated fatty acids as constituent fatty acids and which has been reduced in the contents of environmental pollutants, wherein among the dioxins contained, polychlorinated dibenzoparadioxins (PCDDs) and polychlorinated dibenzofurans (PCDFs) are contained in amounts of less than 0.05 pg-TEQ/g and coplanar PCBs (Co-PCBs) in amounts of less than 0.03 pg-TEQ/g. Also disclosed is a method for producing the highly unsaturated fatty acid or highly unsaturated fatty acid ethyl ester by the steps of removing free fatty acids and environmental pollutants by thin-film distillation from a feedstock oil, ethyl esterifying the resulting fat or oil, and refining the same by rectification and column chromatography.

4 Claims, No Drawings

(56) References Cited

U.S. PATENT DOCUMENTS

| | | |
|---|---|---|
| 2001/0025112 A1 | 9/2001 | Fujita et al. |
| 2001/0042340 A1 | 11/2001 | Tateno et al. |
| 2005/0256326 A1 | 11/2005 | Breivik et al. |
| 2009/0036532 A1 | 2/2009 | Marciacq et al. |
| 2009/0297665 A1 | 12/2009 | Bromley |
| 2010/0267829 A1 | 10/2010 | Breivik et al. |
| 2011/0091947 A1 | 4/2011 | Kim et al. |
| 2011/0130458 A1* | 6/2011 | Breivik .................. A23L 33/12 514/560 |
| 2011/0236364 A1 | 9/2011 | Bromley |
| 2012/0083616 A1 | 4/2012 | Harting Glade et al. |
| 2012/0330043 A1 | 12/2012 | Kelliher et al. |
| 2013/0123525 A1 | 5/2013 | Ikemoto et al. |
| 2013/0131173 A1* | 5/2013 | Griffiths .................. C12N 1/00 514/560 |
| 2014/0200360 A1* | 7/2014 | Kelliher ............. B01D 15/1892 554/193 |
| 2014/0296549 A1* | 10/2014 | Boam ................. B01D 61/027 554/191 |
| 2016/0317592 A1* | 11/2016 | Yamaguchi ............ A61K 8/361 |

FOREIGN PATENT DOCUMENTS

| | | |
|---|---|---|
| EP | 2438819 A1 | 4/2012 |
| JP | S57149400 A | 9/1982 |
| JP | S5888339 A | 5/1983 |
| JP | S60208940 A | 10/1985 |
| JP | H05222392 A | 8/1993 |
| JP | H0633088 A | 2/1994 |
| JP | H08100191 A | 4/1996 |
| JP | 9510091 A | 10/1997 |
| JP | 1095744 A | 4/1998 |
| JP | 10310551 A | 11/1998 |
| JP | 2872986 B1 | 3/1999 |
| JP | 3290152 B | 8/1999 |
| JP | 11209785 A | 8/1999 |
| JP | 2001302584 A | 10/2001 |
| JP | 3400466 B2 | 4/2003 |
| JP | 2988754 B | 9/2003 |
| JP | 3905538 B2 | 1/2007 |
| JP | 2011522913 A | 8/2011 |
| JP | 2012110809 A | 5/2012 |
| JP | 5599187 B2 | 10/2014 |
| WO | 0206430 A1 | 1/2002 |
| WO | 2007107260 A1 | 9/2007 |
| WO | 2008133573 A1 | 11/2008 |
| WO | 2010119319 A1 | 10/2010 |
| WO | 2011080503 A1 | 7/2011 |
| WO | 2011149040 A1 | 12/2011 |
| WO | 2012038833 A1 | 3/2012 |
| WO | 2012109539 A1 | 8/2012 |
| WO | 2015083843 A2 | 6/2015 |

OTHER PUBLICATIONS

JPO Decision on Opposition which was issued on Dec. 20, 2019 by the Japanese Patent Office against the corresponding Japanese patent No. 6309828.

USPTO Final Office Action corresponding to U.S. Appl. No. 16/019,992; dated Dec. 20, 2018.

Breivik, H., et al., Preparation of Highly Purified Concentrates of Eicosapentaenoic acid and Docosahexaenoic acid, 1997, JOACS, vol. 74, No. 11, pp. 1425-1429.

Hideo Kawabe, "Table of Comparison between Invention Disclosed in U.S. Pat. No. 6309828 and Publicly Known Technology," Plaintiffs exhibit No. 16; Mar. 6, 2019.

Kawasaki Jiro; Ministry of Health, Labour and Welfare, "The Japanese Pharmacopoeia", Demandant's exhibit 13, Notice No. 285, 15th edition (Mar. 31, 2006); 5 pages (The Japanese Pharmacopoeia 15th edition (Mar. 31, 2006).

Questions and answers from Professor Masazumi Nishikawa, National University Corporation Miyagi University; Oct. 8, 2018; Plaintiff's Exhibit No. 18.

"Methods of measuring dioxins in food products provisional guideline" (Feb. 2008) Ministry of Health, Labour and Welfare, 46 pages.

"Distillation Systems for Industrial Production," UIC GmbH; pp. 1-13, 2000.

A print-out of the web site of Kyowa Pharmaceutical Industry Co., Ltd., retrieved on Apr. 19, 2019; 11 pages.

Zennegg M, Schmid P., "PCDD/F, PCB, Dioxin-Like PCB, and PBDE in Fish Oil Used As Dietary Supplements in Switzerland", Levels in feed and food, Organohalogen Compounds vol. 68, (2006) pp. 1967-1970.

A print-out of the website of Ministry of Health, Labour and Welfare: On Measures against Dioxins in Foods: Jul. 30, 2008; 40 pages.

Åge Oterhals et al., "Effects of Refining and Removal of Persistent Organic Pollutants by Short-Path Distillation on Nutritional Quality and Oxidative Stability of Fish Oil", J. Agric. Food Chem. 2010, 58, pp. 12250-12269.

Age Oterhals et al., "Modeling of a short-path distillation process to remove persistent organic pollutants in fish oil based on process parameters and quantitative structure properties relationships," Chemosphere, pp. 83-92, 2010.

Åge Oterhals, "Decontamination of persistent organic pollutants in fishmeal and fish oil." Mar. 2011, Dissertation for PhD at the University of Bergen; pp. 1-93.

Anthony P. Bimbo, "Processing of marine oils" 2007, International Fisheries Technology, Kilmarnock, VA, USA; Chapter 4: pp. 77-109.

Berntssen, M.H.G et al., Reducing persistent organic pollutants while maintaining long chain omega-3 fatty acids in farmed Atlantic salmon using decontaminated fish oils for an entire production cycle, 2010, Chemosphere, pp. 242-252.

Bimbo, Anthony P., "Guidelines for Characterizing Food-Grade Fish Oil", INFORM 9 (5), 1998, pp. 473-483.

Breivik, H. et al., Removal of organic environmental pollutants from fish oil by short-path distillation, 2005, Lipid Technology, vol. 17, No. 3, pp. 55-58.

Yushi, "Dioxin is reduced in large quantities by the SPD processing method that constitutes the core of Fine Chemical Dperation", Industrial Report, Nippon Suisan Kaisha, Ltd., vol. 62, No. 11 (2009), pp. 38-39.

Cmolik, Jiri, et al. "Physical Refining of Edible Oils", Eur. J. Lipid Sci. Technol., 102 (2000), pp. 472-486.

Concise Explanation of Relevance for reference 19, (Nikkei Sangyo Shimbun p. 9, published on Aug. 17, 2018), in an opposition against Japanese Patent No. 63096828 an opponent submitted Exhibit 17.

Excerpt from Pharmaceutical Product Interview Form for EPADEL S300, EPADEL S600, EPADEL S900; pp. 1-9, Dec. 2013; Revised Feb. 2017 (4th Edition).

Extended European Search Report corresponding to Application No. 13790465.2-1451/2851361, PCT/JP2013/063425; dated Nov. 30, 2015.

Fournier, Veronique et al., "Thermal degradation of long-chain polyunsaturated fatty acids during deodorization of fish oil", Eur. J. Lipid Sci. Technol., vol. 108 (2006), pp. 33-42.

Hideo Kawabe, Table of Comparison between Invention Disclosed in U.S. Pat. No. 6,309,828 and Publicly Known Technology, Plaintiff exhibit No. 16, Mar. 6, 2019; 7 pages.

Ifoma, "Fish Meal and Fish Oil Dioxin Levels" International Fishmeal & Oil Manufacturers Association, UK, Research Report No. 1999-4, Sep. 1999: 18 pages.

Japanese Industry Standard (JIS), 2008 Method for determination of tetra-through octachlorodibenzo-p-dioxins.

Japan Food Research Laboratories, "European Regulation and Domestic Trend of Bromine-based Retardant", No. 50, Apr. 2006; 8 pages.

Japanese Industrial Standard(JIS), "Method for determination of tetra-through octachlorodibenzo-p-dioxins, tetra-through octachlorodibenzofurans and dioxin-like polychlorinatedbipenyls in industrial water and waste water", Amendment 1, K 0312, 2008.

K. Julshamn et al., "Removal of DDT and Its Metabolites From Fish Oils by Molecular Distillation", Fiskeridirektoratets Skrifter Serie Teknologiske Undersokelser, vol. 5, No. 15 (1973), 10 pp.

Kawasaki Jiro; Ministry of Health, Labour and Welfare, "The Japanese Pharmacopoeia", Demandant's exhibit 13, Notice No. 285, 15th edition (Mar. 31, 2006); 5 pages.

(56) References Cited

OTHER PUBLICATIONS

Kazuhiro Kimata, et al., "Preparation of nitrophenylethylsilylated silica gel and its chromatographic properties in the separation of polychlorinated dibenzo-p-dioxins," Journal of Chromatography 595 (1992) pp. 77-88.
Kenji Tanno et al., "Study on grasp of the food contamination actual situation by dioxin," retrieved from the website of Ministry of Health, Labour and Welfare: On the Results of Surveys including a 2005 Survey of Daily Intakes of Dioxins from Foods, Sep. 26, 2006.
Masazumi Nishikawa, Written Opinion of U.S. Pat. No. 6,309,828: "Method of removing dioxins and brominated flame retardants described in the present patent" National University Corporation Miyagi University, Plaintiff exhibit 17, Sep. 28, 2018; 11 pages.
USPTO Non-Final Office Action corresponding to U.S. Appl. No. 16/019,992; dated Aug. 2, 2018.
USPTO Final Office Action corresponding to U.S. Appl. No. 14/440,652; dated Mar. 4, 2016.
USPTO Non-Final Office Action corresponding to U.S. Appl. No. 14/400,652; dated Aug. 26, 2015.
International Search Report corresponding to Application No. PCT/JP2013/063425; dated Aug. 6, 2013.
Pharmaceutical Product Interview Form for particulate capsules of an ethyl icosapentate preparation, EPAROSE, Jul. 2008.
Ryoji Iwakiri, et al., "Supercritical carbon dioxide extraction to remove PCDD/DFs and coplanar PCBs from fish oil", Journal of Environmental Chemistry vol. 14, No. 2; pp. 253-262, 2004.
Ryuji Yamamura et al., "High purification of polyunsaturated fatty acids", Journal of the Japan Oil Chemists' Society vol. 47 No. 5 (1998) p. 449-456.
Shahidi, Fereidoon, et al., Chemistry of Fatty acids, 2005, Bailey's Industrial Oil and Fat Products, vol. 6, 17 pages.
Tadashi Nakatani, et al., "Contamination Levels of PCDDs, PCDFs and CoPCBs in Fish Oils Used as Raw Materials for Margarine and Shortening and Retailed Fish," J. Food Hyg. Soc. Japan 46(4), Aug. 2005: pp. 169-175.
Takao Fujita, "Studies on Advanced Utilization Technology of Marine Oils", Nippon Suisan Gakkaishi 61(4): 490-493; 14 pages (1995).
Nippon Suisan Kaisha, Ltd., introducing a commerical product of food with functional claims which is a capsule preparation comprising EPA and DHA, Dec. 22, 2017.
Nippon Suisan Kaisha (ltd.) Kashirna Factory, Factory Coverage, "SPD processing method, core of the fine chemical business, greatly reduced dioxins", J. Oleo Sci. vol. 62, No. 11, pp. 38-39 (2009).
Written Opinion corresponding to Application No. 2018-700827; dated May 7, 2019.
Written Opinion corresponding to Application No. JP2018-71685; dated Jul. 27, 2018.
Michiari Kobayashi, Molecular distillation to short path distillation, Transition and reality of short bath distillation (latter part), Chemical Equpment vol. 10. 2008, 12 pages.
Ministry of Health, Labour and Welfare; "Items in Water Quality Standards and their Target Levels (51 Items)", Demandent's exhibit 6, Japan, pulled from Internet <<https://www.mhlw.go.jp/stf/seisakunitsuite/bunya/topics/bukyoku/kenkou/suido/kijun/kijunchi.html Sep. 14, 2018>>.
Ministry of Health, Labour and Welfare; "Summary of investigations into the review of water quality standards" Demandant's exhibit 7, pulled from Internet at <<https://www.mhlw.go.jp/topics/bukoku/kenkou/suido/kijum/konkyo0303.html, 2018>>.
Ministry of Health, Labour and Welfare; Reference No. 12025 "Dioxins"; Demandant's exhibit 8, Test 17; 13 pages, Apr. 2013.
Nao Kodama et al,, "Quality Evaluation of Generic Drugs (1) Sensory Evaluation and Compositions Analyses of Ethyl Eicosapentaenoic Acid Products" Journal of Pharmaceutical Health Care and Sciences 38(4) pp. 228-236 (2012).
NIH Public Access Author Manuscript; Martin van den Berg et al. "The World Health Organization Re-Evaluation of Human and Mammalian Toxic Equivalency Factors for Dioxins and Dioxins-Like Compounds"; Toxicol Sci Oct. 2006; 93(2): 223-241.
Nissui Frontier, "Effective utilization of the bounty of the sea for daily living"; Global, Demandant's exibit 4; issued on Aug. 27, 2009, No. 63, pp. 2-19.
Nissui Umi-no Genki Club; the paper package for IMARK EPA and DHA seamless capsules; Submitted to the Consumer Affairs Agency on Jul. 14, 2016.
Nobushige Doisaki, et al., "Fish oil applications for health care", J. Lipid Nutr. vol. 18, No. 1, pp. 92-101 (2009).
Notice of Reasons for Cancellation corresponding to Application No. 2018-700827; dated Jan. 10, 2019.
Michael Albers et al., "Short Path Distillation in the Fish Oil Industry", UIC GmbH, 2006; 12 pages.
Kumiko Sasaki, "On the 2004 Survey Results of a Survey, etc. of Daily Intake Levels of Dioxins from Foods", Ministry of Health, Labour and Welfare; 21 pp; dated: Feb. 9, 2006.
Reiko Nakagawa, "Shared Study Report from the Health and Labour Science Research Grant", (Project for Promoting the Enhancement of Food Safety), Ministry of Health, Labour and Welfare; pp. 36; dated: Feb. 9, 2006.
"Tips to Better Separation", LC Technical Report, vol. 17, Issue No. 1, Chemicals Evaluation and Research Institute, Japan; pp. 13; dated 2015.

\* cited by examiner

HIGHLY UNSATURATED FATTY ACID OR HIGHLY UNSATURATED FATTY ACID ETHYL ESTER WITH REDUCED ENVIRONMENTAL POLLUTANTS, AND METHOD FOR PRODUCING SAME

CROSS REFERENCE TO RELATED APPLICATIONS

The present application is a continuation of U.S. patent application Ser. No. 15/366,522, filed on Dec. 1, 2016, which is a divisional application of U.S. patent application Ser. No. 14/400,652, filed on Nov. 12, 2014, and issued as U.S. Pat. No. 9,540,306 on Jan. 10, 2017, and which is the U.S. national stage of application No. PCT/JP2013/063425, filed on May 14, 2013, the disclosure of each of which are incorporated herein by reference in their entirety. Priority under 35 U.S.C. § 119(a) and 35 U.S.C. § 365(b) is claimed from Japanese Application No. 2012-110809, filed May 14, 2012, the disclosure of which is also incorporated herein by reference in its entirety.

TECHNICAL FIELD

The present invention relates to a method for reducing the quantities of environmental pollutants, in particular, dioxins, brominated flame retardants, and other substances contained in fats or oils containing the highly unsaturated fatty acids in the production of highly unsaturated fatty acids or highly unsaturated fatty acid ethyl esters from the fats or oils. The present invention further relates to foods, supplements, medicines, cosmetics and feeds that are produced from the fats or oils prepared in accordance with such methods.

BACKGROUND ART

Environmental pollutants typified by dioxins are found almost everywhere on Earth today. They are also known to exert effects on fishes living in polluted ocean areas. They are considered to have no direct effects on health if present in trace amounts but, nevertheless, the ingredients to be ingested by humans as foods or feeds desirably contain the least amounts of environmental pollutants.

Marine product oils, for example, fish oils contain highly unsaturated fatty acids such as EPA (eicosapentaenoic acid, C20:5, n-3, all-cis-5,8,11,14,17-eicosdapentaenoic acid) and DHA (docosahexaenoic acid, C22:6, n-3, all-cis-4,7,10,13,16,19-docosahexaenoic acid). Being known to have various physiological functions, EPA and DHA are used as ingredients of medicines, health foods, foods in general, feeds and the like. Various purification steps are applied to make use of the EPA and/or DHA in marine product oils.

Non-Patent Document 1 discloses removing the insecticide DDT and its metabolites from fish oils by molecular distillation. Non-Patent Document 2 discloses that chlorinated hydrocarbons and free fatty acids can be removed from fats or oils using vacuum stripping or thin-film distillation. Non-Patent Document 3 discloses using physical refining and molecular distillation in order to remove free fatty acids and other undesired substances from oil compositions.

Patent Document 1 and Non-Patent Document 4 each disclose a method for reducing the quantities of environmental pollutants in a mixture containing fats or oils which comprises the step of adding a volatile working fluid to the mixture and the step of subjecting the mixture to at least one stripping process together with the added volatile working fluid.

Non-Patent Document 5 discloses that highly unsaturated fatty acids are decomposed thermally when fish oils are deodorized at high temperatures.

Non-Patent Document 6 discloses removing dioxins, free fatty acids and cholesterols from fish oils by short path distillation so as to make them suitable for use as feedstocks for ethyl esters.

CITATION LIST

Patent Literature

Patent Document 1: Japanese Patent No. 3905538 (WO2004/007654)

Non-Patent Literature

Non-Patent Document 1: K. Julshamn, L. Karlsen and O. R. Braekkan, Removal of DDT and its metabolites from fish oils by molecular distillation, Fiskeridirektoratetsskrifter; Serie teknologiske undersokelser, Vol. 5, No. 15 (1973)
Non-Patent Document 2: Anthony P. Bimbo: Guidelines for characterization of food-grade fish oil. INFORM 9 (5), 473-483 (1998)
Non-Patent Document 3: Jiri Cmolik, Jan Pokorny: Physical refining of edible oils, Eur. J. Lipid Sci. Technol. 102 (7), 472-486 (2000)
Non-Patent Document 4: Harald Breivik, Olav Thorstad: Removal of organic environmental pollutants from fish oil by short-path distillation, Lipid Technology, 17 (3), 55-58 (2005)
Non-Patent Document 5: Veronique Fournier et al.; Thermal degradation of long-chain polyunsaturated fatty acids during deodorization of fish oil, Eur. J. Lipid Sci. Technol., 108, 33-42 (2006)
Non-Patent Document 6: YUSHI, 62(11), 38-39, 2009

SUMMARY OF INVENTION

Technical Problem

An object of the present invention is to provide a method for reducing the quantities of environmental pollutants, in particular, dioxins and brominated flame retardants, contained in fats or oils that contain the highly unsaturated fatty acids as constituent fatty acids in the production of ethyl esters of highly unsaturated fatty acids from the fats or oils; another object of the present invention is to provide ethyl esters having smaller contents of the dioxins and brominated flame retardants.

Solution to Problem

The present invention has been completed on the basis of the finding that if fats or oils in which those highly unsaturated fatty acids that are prone to deteriorate as through oxidation or isomerization are contained as constituent fatty acids are refined by performing molecular distillation or short path distillation under specified conditions, the concentrations of environmental pollutants can be reduced to very low levels while suppressing the deterioration of the highly unsaturated fatty acids. According to this method, the quantities of environmental pollutants in the fats or oils can be reduced in such a way that the total content of dioxins is less than 0.2 pg-TEQ/g where TEQ is short for toxicity equivalency quantity. Further in addition, ethyl esters can be obtained using the thus processed fats or oils as a feedstock. By subjecting the thus obtained ethyl esters to distillation and column chromatographic treatment, the quantities of dioxins in the ethyl esters can be further reduced.

In essence, the present invention relates to the highly unsaturated fatty acids or highly unsaturated fatty acid ethyl esters described below and the methods of producing the same, as well as feeds, foods, medicines, etc. that contain the same.

(1) A highly unsaturated fatty acid or a highly unsaturated fatty acid ethyl ester which has been produced using as a feedstock oil a fat or oil that contains highly unsaturated fatty acids as constituent fatty acids and which has been reduced in the contents of environmental pollutants, wherein among the dioxins contained, polychlorinated dibenzoparadioxins (PCDDs) and polychlorinated dibenzofurans (PCDFs) are contained in amounts of less than 0.05 pg-TEQ/g and coplanar PCBs (Co-PCBs) in amounts of less than 0.03 pg-TEQ/g.

(2) The highly unsaturated fatty acid or highly unsaturated fatty acid ethyl ester according to (1), wherein the content of a brominated flame retardant contained has been reduced to such a level that the amount of BDE-47 is less than 0.18 ng/g, the amount of BDE-100 is less than 0.03 ng/g, the amount of BDE-49 is less than 0.05 ng/g, or the amount of BDE-99 is less than 0.05 ng/g.

(3) The highly unsaturated fatty acid ethyl ester according to (1) or (2), wherein the concentration as occupied by highly unsaturated fatty acids in the sum of fatty acids is at least 80 area %, at least 85 area %, at least 90 area %, at least 95 area %, or at least 96 area %.

(4) The highly unsaturated fatty acid or highly unsaturated fatty acid ethyl ester according to any one of (1) to (3), wherein the fat or oil containing highly unsaturated fatty acids as constituent fatty acids is fish oil, hill oil, marine mammal oil or microorganism oil.

(5) The highly unsaturated fatty acid or highly unsaturated fatty acid ethyl ester according to any one of (1) to (4), wherein the highly unsaturated fatty acid is any one of eicosapentaenoic acid, docosahexaenoic acid, docosapentaenoic acid, dihomo-γ-linoleic acid and arachidonic acid or a combination thereof.

(6) A medicine, supplement or food which comprises the highly unsaturated fatty acid or highly unsaturated fatty acid ethyl ester according to any one of (1) to (5) as an active ingredient.

(7) A method for producing a highly unsaturated fatty acid or a highly unsaturated fatty acid ethyl ester with reduced contents of polychlorinated dibenzoparadioxins (PCDDs), polychlorinated dibenzofurans (PCDFs) and coplanar PCB (Co-PCBs) by the steps of:
a) removing free fatty acids and environmental pollutants by thin-film distillation from a feedstock oil containing highly unsaturated fatty acids as constituent fatty acids;
b) hydrolyzing or ethyl esterifying the resulting highly unsaturated fatty acid containing fat or oil; and
c) refining the same by rectification and column chromatography.

(8) The method according to (7), wherein the content of a brominated flame retardant is also reduced.

(9) The method according to (7) or (8), wherein the concentration as occupied by highly unsaturated fatty acids in the sum of fatty acids in the highly unsaturated fatty acid or highly unsaturated fatty acid ethyl ester is at least 80 area %, at least 85 area %, at least 90 area %, at least 95 area %, or at least 96 area %.

(10) The method according to any one of (7) to (9), wherein the feedstock oil containing highly unsaturated fatty acids as constituent fatty acids is fish oil, hill oil, marine mammal oil or microorganism oil.

(11) The method according to any one of (7) to (10), wherein the thin-film distillation is carried out at a temperature of 200-270° C., 220-260° C., or 220-250° C.

(12) The method according to any one of (7) to (11), wherein the thin-film distillation is carried out at a pressure of 5 Pa or lower, 2 Pa or lower, or 1 Pa or lower.

(13) The method according to any one of (7) to (12), wherein the thin-film distillation is carried out at a flow rate of 20-200 $(kg/h)/m^2$ or 25-120 $(kg/h)/m^2$.

(14) The method according to any one of (7) to (13), wherein the thin-film distillation is molecular distillation or short path distillation.

(15) The method according to any one of (7) to (14), wherein rectification is performed in three or more distillation columns.

(16) The method according to any one of (7) to (15), wherein refining by column chromatography uses column chromatography of reverse-phase distribution type.

(17) A highly unsaturated fatty acid or a highly unsaturated fatty acid ethyl ester that have been produced by the method according to any one of (7) to (16) and whose content of dioxins is less than 0.07 pg-TEQ/g or 0.05 pg-TEQ/g.

(18) The highly unsaturated fatty acid or highly unsaturated fatty acid ethyl ester according to (17), wherein the content of a brominated flame retardant contained has been reduced to such a level that the amount of BDE-47 is less than 0.18 ng/g, the amount of BDE-100 is less than 0.03 ng/g, the amount of BDE-49 is less than 0.05 ng/g, or the amount of BDE-99 is less than 0.05 ng/g.

(19) The highly unsaturated fatty acid or highly unsaturated fatty acid ethyl ester according to (17) or (18), wherein the concentration as occupied by highly unsaturated fatty acids in the sum of fatty acids is at least 80 area %, at least 85 area %, at least 90 area %, at least 95 area %, or at least 96 area %.

(20) A medicine, supplement or food which contains the highly unsaturated fatty acid or highly unsaturated fatty acid ethyl ester according to any one of (17) to (19).

Advantageous Effects of Invention

The method of the present invention ensures that by virtue of distillation at high temperatures in high vacuum over a short period of time, the quantities of environmental pollutants, and dioxins in particular, that are contained in fish oils and the like can be reduced to very low levels without affecting the percentage of highly unsaturated fatty acids in the sum of fatty acids and, hence, it is possible to provide feeds, foods, supplements, medicines and various other products as prepared from fish oils and other feedstocks with which there is no need to worry about contamination by dioxins.

DESCRIPTION OF EMBODIMENTS

On the following pages, the present invention will be described in detail.

As used herein, the term "highly unsaturated fatty acids" refers to fatty acids containing at least 18 carbon atoms and at least 3 double bonds, more preferably fatty acids containing at least 20 carbon atoms and at least 3 or 4 double bonds, and most preferably fatty acids containing at least 20 carbon atoms and at least 5 double bonds. Specific examples include α-linoleic acid (18:3, n-3), γ-linoleic acid (18:3, n-6), dihomo-γ-linoleic acid (20:3, n-6), arachidonic acid (20:4, n-6), eicosapentaenoic acid (20:5, n-3), docosapentaenoic acid (22:5, n-6), docosahexaenoic acid (22:6, n-3), etc.

These are known to be abundant in certain kinds of microorganism oils, vegetable oils, and marine animal oils. Specific examples include: fish oils such as sardine oil, tuna oil, bonito oil, Men Hayden oil, cod liver oil, herring oil, capelin oil, and salmon oil; marine animal oils as from crustaceans such as krill; vegetable oils as from *perilla*, flax, soybean, and rapeseed; fats or oils produced by microorganisms belonging to the genus *Mortierella*, the genus *Penicillium*, the genus *Aspergillus*, the genus *Rhodotorula*, and the genus *Fusarium*.

The method of the present invention is suitable for application to fats or oils derived from marine products with which there are particular concerns about contamination by dioxins, as exemplified by fish oils, krill oil, or marine mammal oils.

As used herein, the term "fats or oils containing highly unsaturated fatty acids as constituent fatty acids" means triglycerides or phospholipids.

If these fats or oils are to be used as feedstock oils in the present invention, preliminary treatments may be performed before they are subjected to molecular distillation or short path distillation. The preliminary treatments may be exemplified by a degumming step, a decoloring step using activated clay or activated charcoal, and a washing step with water.

As used herein, the term "environmental pollutants" embraces: polychlorinated biphenyls (PCBs), DDTs, polychlorinated triphenyls (PCTs), dibenzo-dioxins (PCDDs), and dibenzo-furans (PCDFs); chlorophenols and hexachlorocyclohexanes (HCHs), toxaphenes, dioxins, brominated flame retardants, polyaromatic hydrocarbons (PAHs), organotin compounds (e.g. tributyltin and triphenyltin), organomercury compounds (e.g. methylmercury), etc. To give a guide figure for the degree by which these environmental pollutants have been removed, the sum of dioxins which are representative of the ubiquitous and difficult-to-remove substances is designated in terms of toxic equivalency quantity (pg-TEQ/g).

As used herein, the term "dioxins" refers to the sum of the polychlorinated dibenzoparadioxins (PCDDs), polychlorinated dibenzofurans (PCDFs), and coplanar PCBs (Co-PCBs) that are listed in Table 1 below; the contents of the respective members were measured, each measured value was multiplied by the corresponding toxicity equivalency factor, and summed up to calculate the toxicity equivalency quantity (pg-TEQ/g).

Measurements were also made of brominated flame retardants. The term "brominated flame retardants" collectively refers to the compounds listed in Table 10 below. Although contamination by dioxins in the environment has recently begun to decrease, contamination by brominated flame retardants still tends to increase and hence deserves special note. Applicable indicators are BDE-100, BDE-49, BDE-99, and BDE-47 which are relatively high amount in fish oils.

TABLE 1

Items for Analysis

| | | No. of Cl atoms | Items for Analysis | Abbreviation |
|---|---|---|---|---|
| PCDD | | 4 | 2,3,7,8-tetrachlorodibenzo-p-dioxin | 2,3,7,8-TeCDD |
| | | | Tetrachlorodibenzo-p-dioxins in total | TeCDDs |
| | | 5 | 1,2,3,7,8-pentachlorodibenzo-p-dioxin | 1,2,3,7,8-PeCDD |
| | | | Pentachlorodibenzo-p-dioxins in total | PeCDDs |
| | | 6 | 1,2,3,4,7,8-hexachlorodibenzo-p-dioxin | 1,2,3,4,7,8-HxCDD |
| | | | 1,2,3,6,7,8-hexachlorodibenzo-p-dioxin | 1,2,3,6,7,8-HxCDD |
| | | | 1,2,3,7,8,9-hexachlorodibenzo-p-dioxin | 1,2,3,7,8,9-HxCDD |
| | | | Hexachlorodibenzo-p-dioxins in total | HxCDDs |
| | | 7 | 1,2,3,4,6,7,8-heptachlorodibenzo-p-dioxin | 1,2,3,4,6,7,8-HpCDD |
| | | | Heptachlorodibenzo-p-dioxins in total | HpCDDs |
| | | 8 | Octachlorodibenzo-p-dioxin | OCDD |
| PCDF | | 4 | 2,3,7,8-tetrachlorodibenzofuran | 2,3,7,8-TeCDF |
| | | | Tetrachlorodibenzofurans in total | TeCDFs |
| | | 5 | 1,2,3,7,8-pentachlorodibenzofuran | 1,2,3,7,8-PeCDF |
| | | | 2,3,4,7,8-pentachlorodibenzofuran | 2,3,4,7,8-PeCDF |
| | | | Pentachlorodibenzofurans in total | PeCDFs |
| | | 6 | 1,2,3,4,7,8-hexachlorodibenzofuran | 1,2,3,4,7,8-HxCDF |
| | | | 1,2,3,6,7,8-hexachlorodibenzofuran | 1,2,3,6,7,8-HxCDF |
| | | | 1,2,3,7,8,9-hexachlorodibenzofuran | 1,2,3,7,8,9-HxCDF |
| | | | 2,3,4,6,7,8-hexachlorodibenzofuran | 2,3,4,6,7,8-HxCDF |
| | | | Hexachlorodibenzofurans in total | HxCDFs |
| | | 7 | 1,2,3,4,6,7,8-heptachlorodibenzofuran | 1,2,3,4,6,7,8-HpCDF |
| | | | 1,2,3,4,7,8,9-heptachlorodibenzofuran | 1,2,3,4,7,8,9-HpCDF |
| | | | Heptachlorodibenzofurans in total | HpCDFs |
| | | 8 | Octachlorodibenzofuran | OCDF |
| Co-PCB | Non-ortho form | 4 | 3,4,4',5-tetrachlorobiphenyl | 3,4,4',5-TeCB(#81) |
| | | | 3,3',4,4'-tetrachlorobiphenyl | 3,3',4,4'-TeCB(#77) |
| | | 5 | 3,3',4,4',5-pentachlorobiphenyl | 3,3',4,4',5-PeCB(#126) |
| | | 6 | 3,3',4,4',5,5'-hexachlorobiphenyl | 3,3',4,4',5,5'-HxCB(#169) |
| | Mono-ortho form | 5 | 2',3,4,4',5-pentachlorobiphenyl | 2',3,4,4',5-PeCB(#123) |
| | | | 2,3,4,4',5-pentachlorobiphenyl | 2,3,4,4',5-PeCB(#118) |
| | | | 2,3,3',4,4'-pentachlorobiphenyl | 2,3,3',4,4'-PeCB(#105) |
| | | | 2,3,4,4',5-pentachlorobiphenyl | 2,3,4,4',5-PeCB(#114) |
| | | 6 | 2,3',4,4',5,5'-hexachlorobiphenyl | 2,3',4,4',5,5'-HxCB(#167) |

TABLE 1-continued

Items for Analysis

| No. of Cl atoms | Items for Analysis | Abbreviation |
|---|---|---|
|  | 2,3,3',4,4',5-hexachlorobiphenyl | 2,3,3',4,4',5-HxCB(#156) |
|  | 2,3,3',4,4',5'-hexachlorobiphenyl | 2,3,3',4,4',5'-HxCB(#157) |
| 7 | 2,3,3',4,4',5,5'-heptachlorobiphenyl | 2,3,3',4,4',5,5'-HpCB(#189) |

In the present invention, dioxins are removed by thin-film distillation, preferably by molecular distillation or short path distillation (SPD). Among applicable thin-film distillation methods, one that is performed with the condenser placed within a shorter distance than the mean free path of the vapor molecules evaporating from the heating surface at a specified pressure under a high vacuum (<0.1 Pa) is called molecular distillation. Short path distillation has been developed with a view to enhancing the distilling performance of molecular distillation. Short path distillation is performed at pressures in a medium vacuum region higher than 0.1 Pa, with the condenser placed at distances approximately equal to the mean free path of the evaporating molecules, so it is a practical method that is by far improved in distilling performance than molecular distillation.

In molecular distillation or short path distillation, the feed to be distilled is exposed to high temperatures for such a short period of time that both methods are adapted to removal of unwanted components from triglycerides containing EPA, DHA and other heat-sensitive substances.

In the present invention, molecular distillation or short path distillation is carried out at a temperature of 200-270° C., preferably 220-260° C., and more preferably 220-250° C. Both types of distillation are carried out at a pressure lower than 5 Pa, preferably lower than 2 Pa, and more preferably lower than 1 Pa. They are performed by the thin-film method that is carried out at a flow rate of 20-200 (kg/h)/m$^2$, preferably 25-120 (kg/h)/m$^2$. If the flow volume is unduly small, the productivity will drop, so it is preferred to flow the feedstock oil in a maximum removable volume while ensuring that dioxins are being removed. If distillation is performed under these conditions, highly unsaturated fatty acids, although being heat-sensitive, will suffer little deterioration in quality.

By effecting distillation under these conditions, the quantities of dioxins PCDDs and PCDFs could be reduced to below the limit of measurement, or substantially zero. The value zero typically means less than 0.043 pg-TEQ/g as calculated from the numerical values of detection limit listed in Table 6; in other words, the quantities of dioxins PCDDs and PCDFs can be reduced to less than 0.05 pg-TEQ/g. The quantities of coplanar PCBs can also be reduced to less than 0.2 pg-TEQ/g, even to less than 0.1 pg-TEQ/g, or to less than 0.05 pg-TEQ/g, or to less than 0.02 pg-TEQ/g, and even to less than 0.01 pg-TEQ/g.

As for the brominated flame retardants, if BDE-100, BDE-49, BDE-99 and BDE-47 are chosen as indicators, their quantities can be reduced to less than 0.05 µg/g, preferably less than 0.03 µg/g, and more preferably less than 0.02 µg/g.

Embodiments of the invention method are described below more specifically.

The feedstock oil is preferably one that has been subjected to a degumming process as by washing with water. The washed feedstock oil is immediately subjected to molecular distillation or short path distillation under the conditions described above, so that cholesterols, free fatty acids, environmental pollutants and the like are removed as distillate fractions, yielding the residue containing triglycerides. The residue may be used either immediately or after being subjected to a decoloring process as with activated charcoal or activated clay or to a deodorizing process as by steam distillation. The refined fat or oil thus produced can be used as an ingredient in feeds, foods, or supplements.

The above-mentioned residue may be used as a feedstock for producing ethyl esters containing dioxins in reduced amounts.

To this end, ethyl alcohol and a catalyst or an enzyme are added to the residue and reaction is performed to generate esters of the constituent fatty acids of the triglyceride and the ethyl alcohol. This step of ethyl esterification may be performed by any known method.

If necessary, the formed ethyl ester may be further refined. In order to increase the purity of EPA ethyl ester or DHA ethyl ester, an additional method such as molecular distillation, rectification or column chromatography may be applied. Specifically, refining can be achieved by such methods as disclosed in JP H5-222392 (Family Patent EP0610506), JP H4-41457 (Family Patent EP0460917), JP H6-33088, etc.

Rectification is performed under a high vacuum with three or more distillation columns and the main distillate consisting of the EPA ethyl ester and/or DHA ethyl ester is separated from an initial fraction of the higher volatility and a bottoms fraction of the lower volatility. The conditions of rectification are such that the temperature is in the range of 150-200° C., preferably 160-190° C., more preferably 170-190° C. and the pressure is in the range of 1-300 Pa, preferably 1-200 Pa, more preferably 1-133 Pa. It is preferred that the main distillate of 160-190° C., preferably 170-190° C. is obtained with the degree of vacuum being chosen at 1-133 Pa.

A particularly preferred method is by performing column chromatography after rectification. The present inventors found that as the result of concentrating EPA and DHA by rectification, the relative concentrations of dioxins rose but that by means of subsequent column chromatography, they could be rendered lower than the levels prior to the rectification. While silica gel, ion-exchange resin, activated clay, silver nitrate, etc. may be used in column chromatography, it is particularly preferred to perform column chromatography of reverse-phase distribution type. A reverse-phase distribution system may be created by using, for example, an alkyl group bound silica packing material (e.g. ODS column), with water, alcohols or ketones being used as solvent. Methanol is preferred. These solvents may be used either independently or in admixture.

By combining the above-described techniques of rectification and column chromatography, highly unsaturated fatty acids can be concentrated while reducing the concentrations of environmental pollutants. The concentrations of highly unsaturated fatty acids, say, EPA ethyl ester and/or DHA ethyl ester, can be increased to a purity of at least 80 area %, or at least 85 area %, or at least 90 area %, or 95 area %, or even at least 96 area % while, at the same time, among the dioxins, PCDDs and PCDFs can be reduced in content below their limits of measurement, namely, substantially zero (less than 0.043 pg-TEQ/g as calculated from the detection limits) and the contents of coplanar PCBs can also be lowered to less than 0.1 pg-TEQ/g, or less than 0.03 pg-TEQ/g, or even less than 0.01 pg-TEQ/g. As for the brominated flame retardants, their quantities can be lowered to less than 0.18 ng/g in terms of BDE-47, to less than 0.03 ng/g in terms of BDE-100, to less than 0.05 ng/g in terms of BDE-49, and to less than 0.05 ng/g in terms of BDE-99. The quantities of BDE-100, BDE-49, BDE-99 and BDE-47 can be lowered to less than 0.05 µg/g, preferably less than 0.03 µg/g, more preferably less than 0.02 µg/g. For applications as medicines, the concentration of EPA ethyl ester and/or DHA ethyl ester is preferably equivalent to a purity of at least 96 area %.

The above-described free fatty acids and fatty acid esters that have high concentrations of highly unsaturated fatty acids but low concentrations of environmental pollutants are suitable for use as materials to prepare medicines and supplements that contain the highly unsaturated fatty acids as an active ingredient.

In the case of use for the preparation of medicines and dietary supplements, the EPA and/or DHA in fatty acids need be concentrated to a higher content depending on the need. In that case, the highly unsaturated fatty acids in the glyceride may be concentrated by a method for selective concentration of highly unsaturated fatty acids through lipase reaction (as disclosed in WO2009/17102). Even the thus processed glyceride may be treated by the method of the present invention to have higher concentrations of highly unsaturated fatty acids but lower quantities of environmental pollutants.

The highly unsaturated fatty acid esters produced by the method described above may be hydrolyzed to give the highly unsaturated fatty acids.

On the following pages, Examples of the present invention are described but they are by no means intended to limit the scope of the present invention.

Measurements of Dioxins and Brominated Flame Retardants

In the following Examples of the present invention, a measurement of dioxins was commissioned to JAPAN FOOD RESEARCH LABORATORIES. The method of the measurement was in accordance with the "Provisional Guidelines on the Methods of Measuring Dioxins in Foods (February 2008)" (EISHOKU No. 138 and EINYU No. 200 in 1999).

A measurement of brominated flame retardants was commissioned to "eurofins", a bio-analytical testing company. The method of the measurement was in accordance with high-resolution mass spectrometry (HRGC/HRMS).

Measurement of Acid Value (AV)

In the Examples of the present invention, a measurement of acid value (AV) was conducted in accordance with the JOCS Standard Methods for the Analysis of Fats, Oils and Related Materials (2003 Edition) (compiled by Japan Oil Chemists' Society).

Determining the Composition of Fatty Acids

The composition of fatty acids in a feedstock fish oil and that of fatty acids in the oil resulting from subsequent short path distillation were determined by gas chromatography after ethyl esterification of the fish oil. To be specific, 1 mL of 1 N sodium ethylate/ethanol solution was added to 40 µL of fish oil and the resulting mixture was stirred for about 30 seconds. Subsequently, 1 mL of 1 N hydrochloric acid was added to neutralize the mixture, to which 2 mL of hexane and 3 mL of a saturated aqueous solution of ammonium sulfate were added; after allowing the stirred mixture to settle undisturbed, the upper layer was subjected to measurement by gas chromatography.

Conditions for Gas Chromatographic Analysis

Device type: Agilent 6850 GC system (Agilent Technologies)
Column: DB-WAX J&W 123-7032E
Column temperature: 200° C.
Injection temperature: 300° C.
Injection method: Splitting
Splitting ratio: 100:1
Detector temperature: 300° C.
Detector: FID
Carrier gas: Helium Example 1

Two kinds of crude sardine oil different in acid value and dioxins content were distilled under various conditions to test for the removal of dioxins. The distillation apparatus used was a short path distillation (SPD) device KD 10 (product of UIC GmbH with a distillation surface area of 0.1 $m^2$). The distillation conditions (temperature, pressure, and flow rate) were as shown in Table 2. With the distillation temperature fixed at 250° C., the pressure and flow rate were varied within the ranges of 0.4-3.0 Pa and 25-121 (kg/hr)/$m^2$, respectively.

The dioxins concentrations and acid values of the crude oils and the products of distillation are shown in Table 2.

Irrespective of whether the crude oils had high or low acid values and also irrespective of whether they contained dioxins in large or small quantities, the contents of dioxins could be reduced to less than 0.1 pg-TEQ/g by distillation under all conditions employed.

TABLE 2

| | | Feedstock | | | | | | |
|---|---|---|---|---|---|---|---|---|
| | | Crude sardine oil 1 | | | | Crude sardine oil 2 | | |
| | | Feedstock | Condition | | | Feedstock | Condition | | |
| | | oil 1 | 1 | 2 | 3 | oil 2 | 4 | 5 | 6 |
| PCDD + PCDF | (pg-TEQ/g) | 0.20 | 0.00 | 0.00 | 0.00 | 3.48 | 0.00 | 0.00 | 0.00 |
| Coplaner PCBs | (pg-TEQ/g) | 3.20 | 0.00 | 0.01 | 0.03 | 11.12 | 0.04 | 0.01 | 0.07 |
| Total (of dioxins) | (pg-TEQ/g) | 3.40 | 0.00 | 0.01 | 0.03 | 14.60 | 0.04 | 0.01 | 0.08 |
| Temperature | ° C. | | 250 | 249 | 249 | | 249 | 249 | 249 |
| Pressure | Pa | | 0.7 | 1.3 | 1.5 | | 0.4 | 0.8 | 3.0 |

TABLE 2-continued

| | | Feedstock | | | | | | |
|---|---|---|---|---|---|---|---|---|
| | | Crude sardine oil 1 | | | Crude sardine oil 2 | | | |
| | | Feedstock oil 1 | Condition | | Feedstock oil 2 | Condition | | |
| | | | 1 | 2 | 3 | | 4 | 5 | 6 |
| Flow rate | (kg/h)/m² | | 25 | 78 | 112 | | 30 | 72 | 121 |
| Acid value | | 10.51 | 0.29 | 0.38 | 0.35 | 4.86 | 0.12 | 0.26 | 0.21 |

Example 2

Using the same apparatus as in Example 1, dioxins were removed from semi refined tuna oil (refined by degumming and deacidification) by distillation under the conditions listed in Table 3. As Table 3 shows, the contents of dioxins in the tuna oil could also be reduced to less than 0.1 pg-TEQ/g by the method of the present invention (distilled at a temperature of 250° C., at a pressure of 0.1 Pa, and at a flow rate of 48 (kg/hr)/m²).

Using a different short path distillation (SPD) device KD 6 (product of UIC GmbH with a distillation surface area of 0.06 m²), dioxins were removed from crude sardine oil. As Table 3 shows, the contents of dioxins could also be reduced to less than 0.1 pg-TEQ/g by the method of the present invention (distilled at a temperature of 270° C., at a pressure of 0.6 Pa, and at a flow rate of 20 (kg/hr)/m²).

TABLE 3

| | | Feedstock | | | |
|---|---|---|---|---|---|
| | | Lightly refined tuna oil | | Crude sardine oil 3 | |
| | | Device used | | | |
| | | KD-10 | | KD-6 | |
| | | Feedstock oil 3 | Condition 7 | Feedstock oil 4 | Condition 8 |
| PCDD + PCDF | (pg-TEQ/g) | 1.72 | 0.00 | 0.11 | 0.00 |
| Coplanar PCBs | (pg-TEQ/g) | 7.86 | 0.04 | 7.87 | 0.01 |
| Total (of dioxins) | (pg-TEQ/g) | 9.58 | 0.04 | 7.98 | 0.01 |
| Temperature | ° C. | | 250 | | 270 |
| Pressure | Pa | | 0.1 | | 0.6 |
| Flow rate | (kg/h)/m² | | 48 | | 20 |
| Residue | wt % | | 99.2 | | 92.1 |
| Distilled-off content | wt % | | 0.8 | | 7.9 |
| Acid value | | — | — | 5.79 | 0.14 |

Example 3

Using a centrifugal, molecular distillation apparatus MS380 (product of NIPPON SHARYO, with a distillation surface area of 0.11 m²), dioxins were removed from crude sardine oils by distillation under the conditions listed in Table 4. As Table 4 shows, even the molecular distillation device was capable of reducing the contents of dioxins as in Examples 1 and 2, more specifically to less than 0.2 pg-TEQ/g.

TABLE 4

| | | Feedstock | | | |
|---|---|---|---|---|---|
| | | Crude sardine oil 4 | | Crude sardine oil 5 | |
| | | Feedstock oil 5 | Condition | Feedstock oil 6 | Condition |
| | | | 9 | 10 | | 11 | 12 |
| PCDD + PCDF | (pg-TEQ/g) | 0.17 | 0.10 | 0.03 | 0.09 | 0.05 | 0.00 |
| Coplaner PCBs | (pg-TEQ/g) | 1.12 | 0.05 | 0.00 | 0.52 | 0.01 | 0.00 |
| Total (of dioxins) | (pg-TEQ/g) | 1.29 | 0.15 | 0.03 | 0.61 | 0.07 | 0.00 |
| Temperature | ° C. | | 220 | 240 | | 240 | 260 |
| Pressure | Pa | | 0.67 | 0.67 | | 0.67 | 0.67 |
| Flow rate | (kg/h)/m² | | 182 | 182 | | 182 | 182 |
| Acid value | | 5.61 | 0.31 | 0.12 | 2.85 | 0.17 | 0.11 |

Example 4

A crude sardine oil (with an acid value of 6 and containing 19% EPA and 8% DHA) was washed with warm (85° C.) water (5% relative to the crude oil) and subjected to short path distillation using a short path distillation (SPD) device KD1800 (product of UIC GmbH, with a distillation surface area of 18 m$^2$). The distillation conditions were as follows: degree of vacuum, 0.7-1 Pa; device temperature, 250° C.; feed volume, ca. 2000 kg/H (flow rate: 110 (kg/h)/m$^2$).

The results of measurement of dioxins in oil are shown in Table 5 (for the feedstock oil) and Table 6 (for the SPD oil). The total quantity of dioxins could be reduced from 3.0 pg-TEQ/g to 0.014 pg-TEQ/g in terms of toxicity equivalency quantity. The acid value of the SPD oil was less than 0.2 and there was no change in the composition of fatty acids from the crude oil.

TABLE 5

| | | Items for analysis | Found concentration (pg/g) | Lower limit of detection in sample (pg/g) | Toxicity equivalency factor (TEF) | Toxicity equivalency quantity (TEQ) (pg-TEQ/g) |
|---|---|---|---|---|---|---|
| | PCDD | 2,3,7,8-TeCDD | N.D. | 0.01 | 1 | 0 |
| | | 1,2,3,7,8-PeCDD | 0.03 | 0.01 | 1 | 0.03 |
| | | 1,2,3,4,7,8-HxCDD | N.D. | 0.03 | 0.1 | 0 |
| | | 1,2,3,6,7,8-HxCDD | N.D. | 0.02 | 0.1 | 0 |
| | | 1,2,3,7,8,9-HxCDD | N.D. | 0.03 | 0.1 | 0 |
| | | 1,2,3,4,6,7,8-HpCDD | N.D. | 0.03 | 0.01 | 0 |
| | | OCDD | 0.08 | 0.05 | 0.0003 | 0.000024 |
| | | Total PCDDs | — | — | — | 0.030024 |
| | PCDF | 2,3,7,8-TeCDF | 0.32 | 0.01 | 0.1 | 0.032 |
| | | 1,2,3,7,8-PeCDF (+1,2,3,4,8-PeCDF) | 0.05 | 0.01 | 0.03 | 0.0015 |
| | | 2,3,4,7,8-PeCDF | 0.09 | 0.01 | 0.3 | 0.027 |
| | | 1,2,3,4,7,8-HxCDF (+1,2,3,4,7,9-HxCDF) | 0.02 | 0.02 | 0.1 | 0.002 |
| | | 1,2,3,6,7,8-HxCDF | N.D. | 0.02 | 0.1 | 0 |
| | | 1,2,3,7,8,9-HxCDF | N.D. | 0.03 | 0.1 | 0 |
| | | 2,3,4,6,7,8-HxCDF | N.D. | 0.03 | 0.1 | 0 |
| | | 1,2,3,4,6,7,8-HpCDF | N.D. | 0.02 | 0.01 | 0 |
| | | 1,2,3,4,7,8,9-HpCDF | N.D. | 0.02 | 0.01 | 0 |
| | | OCDF | N.D. | 0.05 | 0.0003 | 0 |
| | | Total PCDFs | — | — | — | 0.0625 |
| | | Total (PCDDs + PCDFs) | — | — | — | 0.092524 |
| Co-PCB | Non-ortho forms | 3,4,4',5-TeCB(#81) | 0.75 | 0.02 | 0.0003 | 0.000225 |
| | | 3,3',4,4'-TeCB(#77) | 82 | 0.05 | 0.0001 | 0.0082 |
| | | 3,3',4,4',5-PeCB(#126) | 28 | 0.04 | 0.1 | 2.8 |
| | | 3,3',4,4',5,5'-HxCB(#169) | 1.9 | 0.02 | 0.03 | 0.057 |
| | | Total Non-ortho forms | 112.65 | — | — | 2.865425 |
| | Mono-ortho forms | 2',3,4,4',5-PeCB(#123) | 19 | 0.4 | 0.00003 | 0.00057 |
| | | 2,3',4,4',5-PeCB(#118) | 1400 | 2 | 0.00003 | 0.042 |
| | | 2,3,3',4,4'-PeCH(#105) | 510 | 0.8 | 0.00003 | 0.0153 |
| | | 2,3,4,4',5-PeCB(#114) | 17 | 0.6 | 0.00003 | 0.00051 |
| | | 2,3',4,4',5,5'-HxCB(#167) | 130 | 0.8 | 0.00003 | 0.0039 |
| | | 2,3,3',4,4',5-HxCB(#156) | 210 | 0.5 | 0.00003 | 0.0063 |
| | | 2,3,3',4,4',5'-HxCH(#157) | 44 | 0.4 | 0.00003 | 0.00132 |
| | | 2,3,3',4,4',5,5'-HpCB(#189) | 24 | 0.4 | 0.00003 | 0.00072 |
| | | Total Mono-ortho forms | 2354 | — | — | 0.07062 |
| | | Total Co-PCBs | 2466.65 | — | — | 2.936045 |
| | | Total dioxins | — | — | — | 3.0 |
| Congeners | PCDD | TeCDDs | N.D. | 0.01 | — | — |
| | | PeCDDs | 0.03 | 0.01 | — | — |
| | | HxCDDs | N.D. | 0.03 | — | — |
| | | HpCDDs | 0.04 | 0.03 | — | — |
| | | OCDD | 0.08 | 0.05 | — | — |
| | | Total PCDDs | 0.15 | — | — | — |
| | PCDF | TeCDFs | 0.43 | 0.01 | — | — |
| | | PeCDFs | 0.14 | 0.01 | — | — |
| | | HxCDFs | 0.02 | 0.03 | — | — |

TABLE 5-continued

| | Feedstock sardine oil Sample lot: 10.09 g | | | |
|---|---|---|---|---|
| Items for analysis | Found concentration (pg/g) | Lower limit of detection in sample (pg/g) | Toxicity equivalency factor (TEF) | Toxicity equivalency quantity (TEQ) (pg-TEQ/g) |
| HpCDFs | N.D. | 0.02 | — | — |
| OCDF | N.D. | 0.05 | — | — |
| Total PCDFs | 0.59 | — | — | — |
| Total (PCDDs + PCDFs) | 0.74 | — | — | — |

Notes:
1. "N.D." refers to the case where the found concentration was less than the lower detection limit.
2. Toxicity equivalency quantity (TEQ) was calculated as if a found concentration less than the lower detection limit was zero.
3. Toxicity equivalency factor (TEF) was in accordance with WHO (2006).
4. 1,2,3,7,8-PeCDF and 1,2,3,4,7,8-HxCDF are cited in total values since they could not be isolated by SP-2331 column.

TABLE 6

| | | Sardine SPD oil Sample lot: 10.04 g | | | |
|---|---|---|---|---|---|
| | Items for analysis | Found concentration (pg/g) | Lower limit of detection in sample (pg/g) | Toxicity equivalency factor (TEF) | Toxicity equivalency quantity (TEQ) (pg-TEQ/g) |
| | PCDD | 2,3,7,8-TeCDD | N.D. | 0.01 | 1 | 0 |
| | | 1,2,3,7,8-PeCDD | N.D. | 0.01 | 1 | 0 |
| | | 1,2,3,4,7,8-HxCDD | N.D. | 0.03 | 0.1 | 0 |
| | | 1,2,3,6,7,8-HxCDD | N.D. | 0.02 | 0.1 | 0 |
| | | 1,2,3,7,8,9-HxCDD | N.D. | 0.03 | 0.1 | 0 |
| | | 1,2,3,4,6,7,8-HpCDD | N.D. | 0.03 | 0.01 | 0 |
| | | OCDD | N.D. | 0.05 | 0.0003 | 0 |
| | | Total PCDDs | — | — | — | 0 |
| | PCDF | 2,3,7,8-TeCDF | N.D. | 0.01 | 0.1 | 0 |
| | | 1,2,3,7,8-PeCDF (+1,2,3,4,8-PeCDF) | N.D. | 0.01 | 0.03 | 0 |
| | | 2,3,4,7,8-PeCDF | N.D. | 0.01 | 0.3 | 0 |
| | | 1,2,3,4,7,8-HxCDF (+1,2,3,4,7,9-HxCDF) | N.D. | 0.02 | 0.1 | 0 |
| | | 1,2,3,6,7,8-HxCDF | N.D. | 0.02 | 0.1 | 0 |
| | | 1,2,3,7,8,9-HxCDF | N.D. | 0.03 | 0.1 | 0 |
| | | 2,3,4,6,7,8-HxCDF | N.D. | 0.03 | 0.1 | 0 |
| | | 1,2,3,4,6,7,8-HpCDF | N.D. | 0.02 | 0.01 | 0 |
| | | 1,2,3,4,7,8,9-HpCDF | N.D. | 0.02 | 0.01 | 0 |
| | | OCDF | N.D. | 0.05 | 0.0003 | 0 |
| | | Total PCDFs | — | — | — | 0 |
| | | Total (PCDDs + PCDFs) | — | — | — | 0 |
| Co-PCB | Non-ortho forms | 3,4,4',5-TeCB(#81) | N.D. | 0.02 | 0.0003 | 0 |
| | | 3,3',4,4'-TeCB(#77) | 0.23 | 0.05 | 0.0001 | 0.000023 |
| | | 3,3',4,4',5-PeCB(#26) | 0.10 | 0.04 | 0.1 | 0.010 |
| | | 3,3',4,4',5,5'-HxCB(#169) | 0.02 | 0.02 | 0.03 | 0.0006 |
| | | Total Non-ortho forms | 0.35 | — | — | 0.010623 |
| | Mono-ortho forms | 2',3,4,4',5-PeCB(#123) | 1.6 | 0.4 | 0.00003 | 0.000048 |
| | | 2,3',4,4',5-PeCB(#118) | 75 | 2 | 0.00003 | 0.00225 |
| | | 2,3,3',4,4'-PeCB(#105) | 18 | 0.8 | 0.00003 | 0.00054 |
| | | 2,3,4,4',5-PeCB(#114) | 1.5 | 0.6 | 0.00003 | 0.000045 |
| | | 2,3',4,4',5,5'-HxCB(#167) | 10 | 0.8 | 0.00003 | 0.00030 |
| | | 2,3,3',4,4',5-HxCB(#156) | 13 | 0.5 | 0.00003 | 0.00039 |
| | | 2,3,3',4,4',5'-HxCB(#157) | 2.8 | 0.4 | 0.00003 | 0.000084 |
| | | 2,3,3',4,4',5,5'-HpCB(#189) | 2.2 | 0.4 | 0.00003 | 0.000066 |
| | | Total Mono-ortho forms | 124.1 | — | — | 0.003723 |
| | | Total Co-PCBs | 124.45 | — | — | 0.014346 |
| | | Total dioxins | — | — | — | 0.014 |

TABLE 6-continued

| | | Sardine SPD oil Sample lot: 10.04 g | | | |
|---|---|---|---|---|---|
| | Items for analysis | Found concentration (pg/g) | Lower limit of detection in sample (pg/g) | Toxicity equivalency factor (TEF) | Toxicity equivalency quantity (TEQ) (pg-TEQ/g) |
| Congeners PCDD | TeCDDs | N.D. | 0.01 | — | — |
| | PeCDDs | N.D. | 0.01 | — | — |
| | HxCDDs | N.D. | 0.03 | — | — |
| | HpCDDs | N.D. | 0.03 | — | — |
| | OCDD | N.D. | 0.05 | — | — |
| | Total PCDDs | 0 | — | — | — |
| PCDF | TeCDFs | N.D. | 0.01 | — | — |
| | PeCDFs | N.D. | 0.01 | — | — |
| | HxCDFs | N.D. | 0.03 | — | — |
| | HpCDFs | N.D. | 0.02 | — | — |
| | OCDF | N.D. | 0.05 | — | — |
| | Total PCDFs | 0 | — | — | — |
| | Total (PCDDs + PCDFs) | 0 | — | — | — |

Notes:
1. "N.D." refers to the case where the found concentration was less than the lower detection limit.
2. Toxicity equivalency quantity (TEQ) was calculated as if a found concentration less than the lower detection limit was zero.
3. Toxicity equivalency factor (TEF) was in accordance with WHO (2006).
4. 1,2,3,7,8-PeCDF and 1,2,3,4,7,8-HxCDF are cited in total values since they could not be isolated by SP-2331 column.

Example 5

Crude sardine oil was subjected to short path distillation under the same conditions as in Example 4 and the composition of fatty acids was determined by the previously described method both before and after the distillation. The results are shown in Table 7. For fatty acids that had 18 or more carbon atoms with 3 or more double bonds and which were prone to oxidize, isomerize or otherwise deteriorate upon heating, the proportions of such fatty acids in the total fatty acids in the feedstock oil and the SPD oil, as well as the changes in such proportions are shown in the table. Each of the fatty acids under examination suffered only a little change in content and even those fatty acids with the greater number of double bonds did not experience any particularly great variations. From these results, it was verified that the method of the present invention is a good way to remove dioxins without causing deterioration of highly unsaturated fatty acids. In Table 7, ARA stands for arachidonic acid and DPA docosapentaenoic acid.

washing with warm water, the ethyl ester was dried and rectified with a degree of vacuum of 13 Pa to give the main distillate (with a temperature of ca. 176° C.), which was treated by HPLC using column of reverse-phase distribution type (ODS); the solvent was subsequently distilled off to yield an ethyl ester of 97% pure EPA.

The contents of dioxins in this ethyl ester were measured by the same method as in Example 4 and the results are shown in Table 8. No dioxins would be concentrated during the ethyl esterification and the subsequent refining step; use of the feedstock treated as in Example 4 enabled the production of EPA's ethyl ester samples in which the total quantity of dioxins was less than 0.07 pg-TEQ/g in terms of toxicity equivalency quantity. The data in Table 8 are for the production from three different lots of feedstock. It was verified that the method of the present invention enabled consistent production of EPA's ethyl ester samples in which

TABLE 7

| | C18:3 n-6 | C18:3 n-3 | C18:4 n-3 | ARA | C20:4 n-3 | EPA | DPA | DHA |
|---|---|---|---|---|---|---|---|---|
| Feedstock oil (area %) | 0.65 | 0.62 | 2.55 | 1.25 | 0.85 | 21.89 | 2.60 | 7.67 |
| After distillation (area %) | 0.63 | 0.57 | 2.53 | 1.26 | 0.86 | 21.86 | 2.62 | 7.65 |
| Relative change (After distillation − Feedstock oil) | −0.02 | −0.05 | −0.03 | 0.01 | 0.01 | −0.03 | 0.02 | −0.01 |

Example 6

An ethyl ester of EPA was produced from the distilled oil as prepared in Example 4.

The production procedure was as follows: the SPD oil was subjected to ethanolysis reaction with ethyl alcohol in the presence of an alkali catalyst to form an ethyl ester; after the total quantity of dioxins was between 0.006 and 0.021 pg-TEQ/g in terms of toxicity equivalency quantity. As for NDs below the detection limit, calculation was made by inserting numeric values of detection limit and yet the increase was only 0.005 in numerical value, meaning that it is possible to produce EPA's ethyl ester samples with 0.011-0.026 pg-TEQ/g.

TABLE 8

| | | Toxicity equivalency factor(TEF) | Lot. 1 | | Lot. 2 | | Lot. 3 | |
|---|---|---|---|---|---|---|---|---|
| | | | Found concentration (pg/g) | Toxicity equivalency quantity (pg-TEQ/g) | Found concentration (pg/g) | Toxicity equivalency quantity (pg-TEQ/g) | Found concentration (pg/g) | Toxicity equivalency quantity (pg-TEQ/g) |
| PCDD | 2,3,7,8-TCDD | 1 | N.D. | 0 | N.D. | 0 | N.D. | 0 |
| | 1,2,3,7,8-PeCDD | 1 | N.D. | 0 | N.D. | 0 | N.D. | 0 |
| | 1,2,3,4,7,8-HxCDD | 0.1 | N.D. | 0 | N.D. | 0 | N.D. | 0 |
| | 1,2,3,6,7,8-HxCDD | 0.1 | N.D. | 0 | N.D. | 0 | N.D. | 0 |
| | 1,2,3,7,8,9-HxCDD | 0.1 | N.D. | 0 | N.D. | 0 | N.D. | 0 |
| | 1,2,3,4,6,7,8-HpCDD | 0.01 | N.D. | 0 | N.D. | 0 | N.D. | 0 |
| | OCDD | 0.0003 | N.D. | 0 | N.D. | 0 | N.D. | 0 |
| PCDF | 2,3,7,8-TCDF | 0.1 | N.D. | 0 | N.D. | 0 | N.D. | 0 |
| | 1,2,3,7,8-PeCDF | 0.03 | N.D. | 0 | N.D. | 0 | N.D. | 0 |
| | 2,3,4,7,8-PeCDF | 0.3 | N.D. | 0 | N.D. | 0 | N.D. | 0 |
| | 1,2,3,4,7,8-HxCDF | 0.1 | N.D. | 0 | N.D. | 0 | N.D. | 0 |
| | 1,2,3,6,7,8-HxCDF | 0.1 | N.D. | 0 | N.D. | 0 | N.D. | 0 |
| | 1,2,3,7,8,9-HxCDF | 0.1 | N.D. | 0 | N.D. | 0 | N.D. | 0 |
| | 2,3,4,6,7,8-HxCDF | 0.1 | N.D. | 0 | N.D. | 0 | N.D. | 0 |
| | 1,2,3,4,6,7,8-HpCDF | 0.01 | N.D. | 0 | N.D. | 0 | N.D. | 0 |
| | 1,2,3,4,7,8,9-HpCDF | 0.01 | N.D. | 0 | N.D. | 0 | N.D. | 0 |
| | OCDF | 0.0003 | N.D. | 0 | N.D. | 0 | N.D. | 0 |
| total PCDDs + PCDFs | | | | 0 | | 0 | | 0 |
| Coplanar PCB | Non-ortho forms 3,3',4,4'-TeCB (#77) | 0.0001 | 0.82 | 0.000082 | 0.54 | 0.000054 | 0.45 | 0.000045 |
| | 3,4,4',5-TeCB (#81) | 0.0003 | N.D. | 0 | N.D. | 0 | N.D. | 0 |
| | 3,3',4,4',5-PeCB (#126) | 0.1 | N.D. | 0 | N.D. | 0 | N.D. | 0 |
| | 3,3',4,4',5,5'-HxCB (#169) | 0.03 | N.D. | 0 | N.D. | 0 | N.D. | 0 |
| | Mono-ortho forms 2,3,3',4,4'-PeCB (#105) | 0.0003 | 66 | 0.0198 | 19 | 0.0057 | 31 | 0.0093 |
| | 2,3,4,4',5-PeCB (#114) | 0.0003 | N.D. | 0 | N.D. | 0 | N.D. | 0 |
| | 2,3',4,4',5-PeCB (#118) | 0.0003 | 3.1 | 0.00093 | 0.45 | 0.000135 | 1.2 | 0.00036 |
| | 2',3,4,4',5-PeCB (#123) | 0.0003 | N.D. | 0 | N.D. | 0 | N.D. | 0 |
| | 2,3,3',4,4',5-HxCB (#156) | 0.0003 | N.D. | 0 | N.D. | 0 | N.D. | 0 |
| | 2,3,3',4,4',5-HxCB (#157) | 0.0003 | N.D. | 0 | N.D. | 0 | N.D. | 0 |
| | 2,3',4,4',5,5'-HxCB (#167) | 0.0003 | N.D. | 0 | N.D. | 0 | N.D. | 0 |
| | 2,3,3',4,4',5,5'-HpCB (#189) | 0.0003 | N.D. | 0 | N.D. | 0 | N.D. | 0 |
| total coplaner PCBs | | | | 0.020812 | | 0.005889 | | 0.009705 |
| total TEQ(pg-TEQ/g) | | | | 0.021 | | 0.006 | | 0.010 |

Example 7

The rectification and column chromatographic processing in the refining step after ethyl esterification were verified for possible effects they might have on the concentration of dioxins. The feedstock oil was sardine oil that was simply diacidified and decolored without subsequent thin-film distillation. This was because use of fats or oils containing more dioxins would provide greater ease in observing the possible effects of the refining process.

The feedstock oil was ethyl esterified using an alkali catalyst. The resulting ethyl esters were first subjected to a rectification step, thereby collecting fractions containing ethyl esters of C20 fatty acids. Subsequently, a fraction of eicosapentaenoic acid ethyl ester was collected by ODS column chromatography.

At the respective stages, the contents of dioxins were measured.

Table 9 shows data for the four components that experienced greater variations (in terms of absolute value and toxicity equivalency quantity) and the total of dioxins (in toxicity equivalency quantity). The rectification step caused the components #105 and #118 to be concentrated by far greater degrees than when they were just after the esterification. On the other hand, the content of #77 decreased rather than increased. It is assumed that in rectification, ethyl esters of eicosapentaenoic acid and other fatty acids behaved in a similar way to dioxins, so that the dioxins were concentrated as were the ethyl esters of eicosapentaenoic acid and other fatty acids.

Upon column treatment, the content of #77 remained substantially the same or increased a little whereas the contents of other components dropped considerably. It is assumed that in the column treatment, ethyl esters and dioxins behaved in a sufficiently different way to enable separation of the two components.

Therefore, by combining rectification with the column treatment, the concentrating of the desired ethyl esters and the reduction of dioxins levels can be achieved simultaneously.

TABLE 9

| | Non-ortho 3,3'4,4'-TeCB (#77) | Non-ortho 3,3'4,4',5-PeCB (#126) | Mono-ortho 2,3,3',4,4'-PeCB (#105) | Mono-ortho 2,3',4,4',5-PeCB (#118) | Total dioxins |
|---|---|---|---|---|---|
| As esterified | 380 pg/g (0.038 pg-TEQ/g) | 82 pg/g (8.2 pg-TEQ/g) | 4700 pg/g (0.47 pg-TEQ/g) | 9700 pg/g (0.97 pg-TEQ/g) | (10.62 pg-TEQ/g) |

TABLE 9-continued

|  | Non-ortho 3,3'4,4'-TeCB (#77) | Non-ortho 3,3'4,4',5-PeCB (#126) | Mono-ortho 2,3,3',4,4'-PeCB (#105) | Mono-ortho 2,3',4,4',5-PeCB (#118) | Total dioxins |
|---|---|---|---|---|---|
| As rectified | 250 (0.025) | 170 (17) | 24000 (2.4) | 30000 (3) | (23.44) |
| As column treated | 260 (0.026) | 0.69 (0.069) | 3700 (0.37) | 180 (0.018) | (0.48) |

Example 8

Crude sardine oil as feedstock was distilled by SPD as in Example 4 to give an SPD oil, which was ethyl esterified and refined by the same procedures as in Example 6 to yield EPA ethyl esters. They were measured for the contents of brominated flame retardants. The measurement was commissioned to the bio-analytical testing company "eurofins". The results are shown in Table 10. The contents of the respective brominated flame retardants in the feedstock sardine oil had been reduced to less than their detection limits. All of BDE-100, BDE-49, BDE-99, BDE-47, BDE-28, BDE-66, and BDE-154 that were contained in the feedstock oil in amounts equal to or greater than their detection limits had been reduced in concentration and, in particular, the concentrations of BDE-100, BDE-49, BDE-99 and BDE-47 were verified to have dropped distinctly.

TABLE 10

|  | Sardine oil | SPD oil | Ethyl ester |
|---|---|---|---|
| CYR11 HBCD (hexabromocyclododecane) | | | |
| Hexabromocyclododecane HBCD (total of a, b, and g forms) | <2.0 ng/g | <2.0 ng/g | <2.0 ng/g |
| CYR16 pbb (polybrominated biphenyls) | | | |
| 2,2',3,3',4,4',5,5',6-nonabromobenzene # BB 206 | <0.218 ng/g | <0.216 ng/g | <0.222 ng/g |
| 2,2',3,3',4,4',5,5'-octabromobenzene # BB 194 | <0.109 ng/g | <0.108 ng/g | <0.111 ng/g |
| 2,2',3,4,4',5,5'-heptabromobenzene # BB 180 | <0.0544 ng/g | <0.0541 ng/g | <0.0554 ng/g |
| 2,2',4,4',5,5'-hexabromobenzene # 153 | <0.0326 ng/g | <0.0325 ng/g | <0.0333 ng/g |
| 2,2',4,5,5'-pentabromobenzene # 101 | <0.0218 ng/g | <0.0216 ng/g | <0.0222 ng/g |
| 2,2',5,5'-tetrabromobenzene # 52 | <0.0109 ng/g | <0.0108 ng/g | <0.0111 ng/g |
| decabromobenzene # 209 | <0.544 ng/g | <0.541 ng/g | <0.554 ng/g |
| Total of bromobenzenes (X) | 0.990 ng/g | 0.985 ng/g | 1.01 ng/g |
| Total of bromobenzenes (X·X) | ND ng/g | ND ng/g | ND ng/g |
| CYR21 PBDE (LR) | | | |
| 2,2',3,3',4,4',5,5',6-nonabromodiphenyl ether (BDE-206) | <0.218 ng/g | <0.216 ng/g | <0.222 ng/g |
| 2,2',3,3',4,4',6,6'-octabromodiphenyl ether (BDE-197) | <0.109 ng/g | <0.108 ng/g | <0.111 ng/g |
| 2,2',3,3'4,4',5,6,6'-nonabromodiphenyl ether (BDE-207) | <0.218 ng/g | <0.216 ng/g | <0.222 ng/g |
| 2,2',3,3,4,4',5,5',6-octabromodiphenyl ether (BDE-196) | <0.109 ng/g | <0.108 ng/g | <0.111 ng/g |
| 2,2',3,4,4',5-hexabromodiphenyl ether (BDE-138) | <0.0326 ng/g | <0.0325 ng/g | <0.0333 ng/g |
| 2,2',3,4,4',6,6'-heptabromodiphenyl ether (BDE-184) | <0.0544 ng/g | <0.0541 ng/g | <0.0554 ng/g |
| 2,2',4,4',5,6'-hexabromodiphenyl ether (BDE-154) | 0.0384 ng/g | <0.0325 ng/g | <0.0333 ng/g |
| 2,2',4,4',6-pentabromodiphenyl ether (BDE-100) | 0.0691 ng/g | <0.0216 ng/g | <0.0222 ng/g |
| 2,2',4,5'-tetrabromodiphenyl ether (BDE-49) | 0.108 ng/g | <0.0108 ng/g | <0.0111 ng/g |
| 2,2',4-tribromodiphenyl ether (BDE-17) | 0.0118 ng/g | <0.0108 ng/g | <0.0111 ng/g |
| 2,2',3,4,4',5',6-heptabromodiphenyl ether (BDE-183) | <0.0544 ng/g | <0.0541 ng/g | <0.0554 ng/g |
| 2,2',3,4,4'-pentabromodiphenyl ether (BDE-85) | <0.0218 ng/g | <0.0216 ng/g | <0.0222 ng/g |
| 2,2',4,4',5,5'-hexabromodiphenyl ether (BDE-153) | <0.0326 ng/g | <0.0325 ng/g | <0.0333 ng/g |
| 2,2',4,4',5-pentabromodiphenyl ether (BDE-99) | 0.0994 ng/g | <0.0216 ng/g | <0.0222 ng/g |
| 2,2',4,4'-tetrabromodiphenyl ether (BDE-47) | 0.354 ng/g | 0.0131 ng/g | <0.0111 ng/g |
| 2,3,3',4,4',5',6-heptabromodiphenyl ether (BDE-191) | <0.0544 ng/g | <0.0541 ng/g | <0.0554 ng/g |
| 2,3,3',4,4',5-hexabromodiphenyl ether (BDE-156) | <0.0326 ng/g | <0.0325 ng/g | <0.0333 ng/g |
| 2,3',4,4',6-pentabromodiphenyl ether (BDE-119) | <0.0218 ng/g | <0.0216 ng/g | <0.0222 ng/g |
| 2,3',4,4'-tetrabromodiphenyl ether (BDE-66) | 0.0281 ng/g | <0.0108 ng/g | <0.0111 ng/g |
| 2,3',4',6-tetrabromodiphenyl ether (BDE-77) | <0.0109 ng/g | <0.0108 ng/g | <0.0111 ng/g |
| 2,4,4'-tribromodiphenyl ether (BDE-28) | 0.0251 ng/g | <0.0108 ng/g | <0.0111 ng/g |
| 3,3',4,4',5-pentabromodiphenyl ether (BDE-126) | <0.0218 ng/g | <0.0216 ng/g | <0.0222 ng/g |
| 3,3',4,4'-tetrabromodiphenyl ether (BDE-71) | <0.0109 ng/g | <0.0108 ng/g | <0.0111 ng/g |
| Total of octabromodiphenyl ethers (X) | 0.218 ng/g | 0.216 ng/g | 0.222 ng/g |
| Total of octabromodiphenyl ethers (X·X) | ND ng/g | ND ng/g | ND ng/g |
| Decabromodiphenyl ether (BDE-209) | <1.09 ng/g | <1.08 ng/g | <1.11 ng/g |
| Total of tetrabromodiphenyl ethers (X) | 0.513 ng/g | 0.0564 ng/g | 0.0554 ng/g |
| Total of tetrabromodiphenyl ethers (X·X) | 0.491 ng/g | 0.0131 ng/g | ND ng/g |
| Total of tribromodiphenyl ethers (X) | 0.0369 ng/g | 0.0216 ng/g | 0.0222 ng/g |
| Total of tribromodiphenyl ethers (X·X) | 0.0369 ng/g | ND ng/g | ND ng/g |
| Total of nonabromodiphenyl ethers (X) | 0.435 ng/g | 0.433 ng/g | 0.443 ng/g |
| Total of nonabromodiphenyl ethers (X·X) | ND ng/g | ND ng/g | ND ng/g |
| Total of bromodiphenyl ethers (X) | 2.82 ng/g | 2.21 ng/g | 2.26 ng/g |
| Total of bromodiphenyl ethers (X·X) | 0.735 ng/g | 0.0131 ng/g | ND ng/g |
| Total of hexabromodiphenyl ethers (X) | 0.136 ng/g | 0.130 ng/g | 0.133 ng/g |
| Total of hexabromodiphenyl ethers (X·X) | 0.0384 ng/g | ND ng/g | ND ng/g |
| Total of heptabromodiphenyl ethers (X) | 0.163 ng/g | 0.162 ng/g | 0.166 ng/g |
| Total of heptabromodiphenyl ethers (X·X) | ND ng/g | ND ng/g | ND ng/g |

TABLE 10-continued

| | Sardine oil | SPD oil | Ethyl ester |
|---|---|---|---|
| Total of pentabromodiphenyl ethers (✕) | 0.234 ng/g | 0.108 ng/g | 0.111 ng/g |
| Total of pentabromodiphenyl ethers (✕✕) | 0.169 ng/g | ND ng/g | ND ng/g |
| CYR26 TBBPA (tetrabromobisphenol A) | | | |
| tetrabromobisphenol A (✕✕) | <0.538 ng/g | <0.544 ng/g | <0.544 ng/g |

(✕) = (calculated in terms of quantification limit)
(✕✕) = (values less than the quantification limit are deleted)

INDUSTRIAL APPLICABILITY

According to the present invention, the amounts of environmental contaminants, especially dioxins and brominated flame retardants, that are contained in fats or oils that comprise highly unsaturated fatty acids as constituent fatty acid, as exemplified by fish oils containing EPA and DHA can be markedly reduced, making it possible to provide fats or oils having this feature. The products thus obtained are suitable for use in feeds, foods, supplements, medicines, and the like.

The invention claimed is:

1. A composition comprising a highly unsaturated fatty acid ethyl ester which has been produced using as a feedstock oil or fat that contains (i) the highly unsaturated fatty acid as a constituent fatty acid, and (ii) brominated flame retardant,
    wherein the composition comprises brominated flame retardant comprising tetrabromodiphenyl ethers,
    wherein the amount of the brominated flame retardant has been reduced to such a level that a total amount of the tetrabromodiphenyl ethers is up to 0.0554 ng/g,
    wherein the tetrabromodiphenyl ether consists of 2,2',4,5'-tetrabromodiphenyl ether (BDE-49), 2,2',4,4'-tetrabromodiphenyl ether (BDE-47), 2,3',4,4'-tetrabromodiphenyl ether (BDE-66), 2,3',4',6-tetrabromodiphenyl ether (BDE-71), and 3,3',4,4'-tetrabromodiphenyl ether (BDE-77),
    wherein the highly unsaturated fatty acid comprises eicosapentaenoic acid, and
    wherein the concentration of eicosapentaenoic acid in the sum of constituent fatty acids in the composition is at least 80 area %.

2. The composition according to claim 1, wherein the concentration of eicosapentaenoic acid in the sum of constituent fatty acids in the composition is at least 85 area %, at least 90 area %, at least 95 area %, or at least 96 area %.

3. The composition according to claim 1, wherein the fat or oil is fish oil, krill oil, marine mammal oil, or microorganism oil.

4. A medicine, supplement, food, cosmetics, or feeds which comprises the composition according to claim 1 as an active ingredient.

* * * * *